United States Patent
Bayer et al.

(10) Patent No.: US 9,803,171 B2
(45) Date of Patent: Oct. 31, 2017

(54) METHOD FOR MAKING DEHYDRATED MYCELIUM ELEMENTS AND PRODUCT MADE THEREBY

(71) Applicants: Eben Bayer, Troy, NY (US); Gavin McIntyre, Troy, NY (US); Sarah Araldi, Troy, NY (US)

(72) Inventors: Eben Bayer, Troy, NY (US); Gavin McIntyre, Troy, NY (US); Sarah Araldi, Troy, NY (US)

(73) Assignee: Ecovative Design LLC, Green Island, NY (US)

(*) Notice: Subject to any disclaimer, the term of this patent is extended or adjusted under 35 U.S.C. 154(b) by 379 days.

(21) Appl. No.: 13/865,321

(22) Filed: Apr. 18, 2013

(65) Prior Publication Data

US 2013/0280791 A1   Oct. 24, 2013

Related U.S. Application Data

(63) Continuation-in-part of application No. 12/001,556, filed on Dec. 12, 2007, and a continuation-in-part of application No. 13/454,856, filed on Apr. 24, 2012.

(51) Int. Cl.
| | | |
|---|---|---|
| *C12N 1/00* | (2006.01) | |
| *C12N 1/14* | (2006.01) | |
| *A01G 1/04* | (2006.01) | |
| *C05D 9/00* | (2006.01) | |
| *C12N 11/14* | (2006.01) | |

(52) U.S. Cl.
CPC ............ *C12N 1/14* (2013.01); *A01G 1/046* (2013.01); *C05D 9/00* (2013.01); *C12N 11/14* (2013.01)

(58) Field of Classification Search
None
See application file for complete search history.

(56) References Cited

PUBLICATIONS

Amsellem et al., Crop Protection, 1999, vol. 18, p. 643-649.*
Mushroom Growers' Handbook 2, Shiitake Cultivation, Part I Shiitake, 2005, Published by Mush World, p. 73-90.*
Growers' Handbook 2, Shiitake Cultivation, Part I Shiitake (2005, Published by Mush World, pp. 27-35.*
"Mycelium Running: How Mushrooms Can Help Save the World", Paul Stamets, 2005, Ten Speed press, p. 189 Only.*

* cited by examiner

*Primary Examiner* — Kade Ariani
(74) *Attorney, Agent, or Firm* — Francis C. Hand; Carella, Byrne et al.

(57) ABSTRACT

A living hydrated mycelium composite containing at least one of a combination of mycelium and fibers, mycelium and particles, and mycelium, particles and fibers is processed with a nutrient material to promote mycelia tissue growth; thereafter dehydrated to a moisture content of less than 50% by weight to deactivate the further growth of mycelia tissue; and then stored. The stored dehydrated mycelium composite is further processed by rehydrating to reactivate the mycelium and to initiate growth of at least one fruiting body.

1 Claim, 5 Drawing Sheets

METHOD FOR MAKING DEHYDRATED MYCELIUM ELEMENTS AND PRODUCT MADE THEREBY

This application is a continuation-in-part of Ser. No. 12/001,556, filed Dec. 12, 2007 and a continuation-in-part of Ser. No. 13/454,856, filed Apr. 24, 2012.

This invention relates to a method for making dehydrated mycelium elements and a product made thereby. More particularly, this invention relates to a method of making dehydrated mycelium elements for growing mushrooms.

As is known from published United States Patent Application 2008/0145577, use can be made of a fungus to form composite materials by mixing an inoculum including a preselected fungus with discrete particles and a nutrient material capable of being digested by the fungus. It is also known from U.S. Pat. No. 8,001,719 to enclose and grow a fungal primordium in a mold to obtain a mass of fungal tissue in the form of low density chitinous material.

As is also known from published United States Patent Application 2102/0270302, dehydrated mycelium elements can be made for use as is or in the subsequent fabrication of various shaped parts.

It is an object of this invention to provide a method for the production of dehydrated mycelium elements particularly for the growing of mushrooms.

It is another object of this invention to produce dehydrated mycelium pellets that can be used as is or can be used to make formed elements from which mushrooms may grow upon being re-hydrated.

Briefly, the invention provides a method for producing dehydrated mycelium which can be re-hydrated and rapidly re-formed into many different shapes, such as bricks, blocks, pellets and the like elements wherein the adhesion of the elements is achieved through re-animation of a fungal organism which grows the elements together.

In one embodiment, the invention provides a method of making dehydrated mycelium elements comprising the steps of creating a living hydrated mycelium composite containing at least one of a combination of mycelium and fibers, mycelium and particles, and mycelium, particles and fibers; adding a nutrient material to the mycelium composite in an amount to promote mycelia tissue growth; thereafter dehydrating the mycelium composite to a moisture content of less than 50% by weight to deactivate the further growth of mycelia tissue; and thereafter storing the dehydrated mycelium composite at a temperature in the range of from −50° F. to +200° F.

The dehydrated mycelium composite may be processed into a plurality of discrete particles or coated fibers for storage.

In accordance with the invention, the stored dehydrated mycelium composite is taken out of storage and further processed by re-hydrating the composite to reactivate the mycelium and to initiate growth of at least one fruiting body. In this embodiment, after removing from storage, the dehydrated mycelium composite is pelletized into a plurality of particles and aggregated into a container. The container is then sealed and transported, for example, to a retail site for sale to patrons for the growing of mushrooms at home or elsewhere.

In an alternative step, the dehydrated mycelium composite may be pelletized and formed into a block which is then encased in a protective coating, such as a wax coating, or a sprayed on coating, for transportation to a retail site for sale.

In order to initiate growth, the container or coating as the case may be is opened to obtain access to the dehydrated composite material and in an environment at ambient temperatures, that is at normal room temperatures, and without need for a darkened place. Next, moisture is applied through the opening in the container or coating. For example, the moisture may be sprayed onto the exposed surfaces of the dehydrated composite material or poured on. After a suitable period of time, one or more fruiting bodies (i.e. mushrooms) will begin to grow through the opening in the container or coating.

Typically, the dehydrated composite material in the container will produce at least two growths (crops) of mushrooms over time before exhaustion.

These and other objects and advantages of the invention will become more apparent from the following detailed description taken in conjunction with the accompanying drawings wherein.

Figure 2:
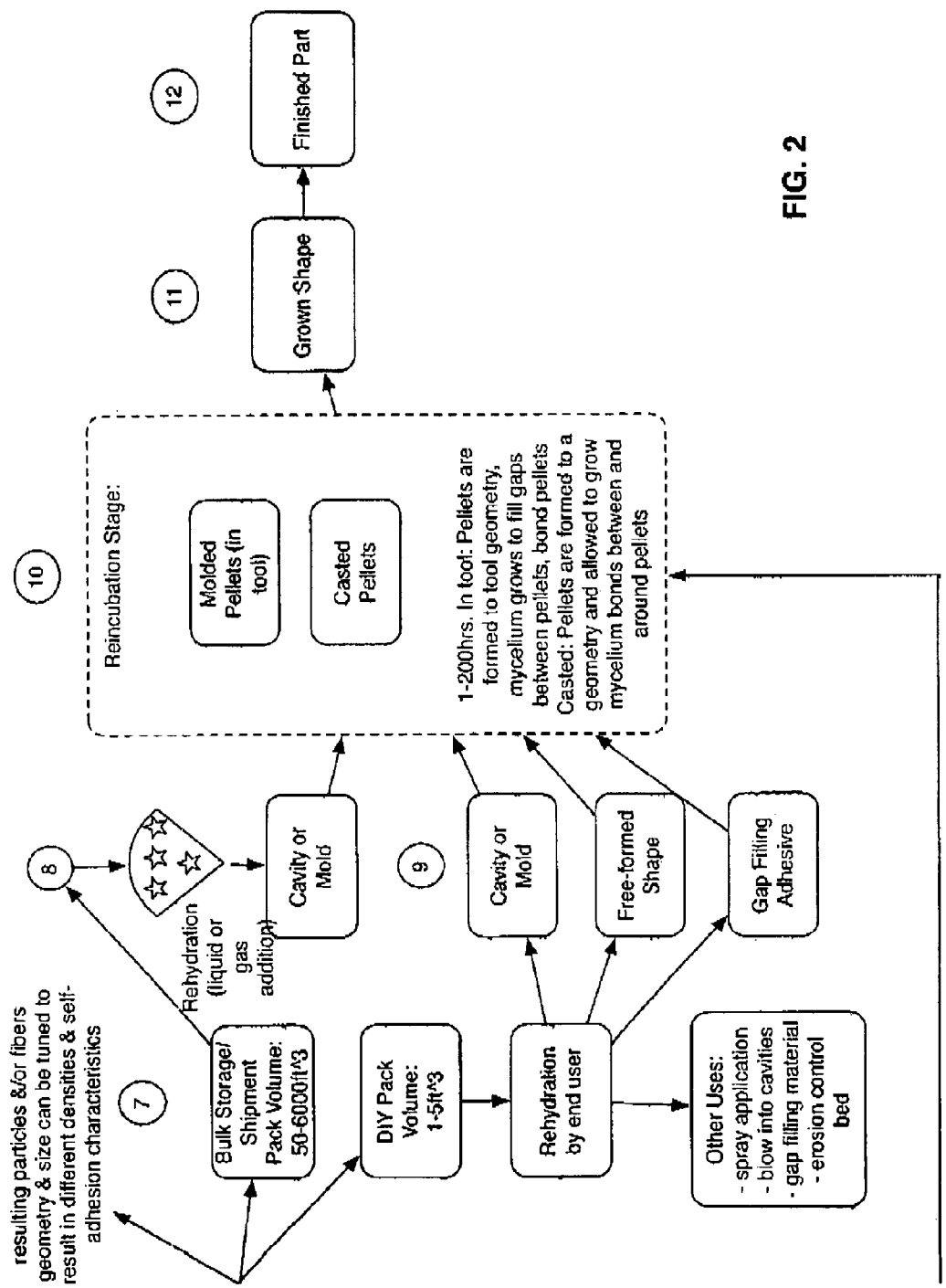
FIG. 2 illustrates further steps in the method of FIG. 1.
Figure 3:
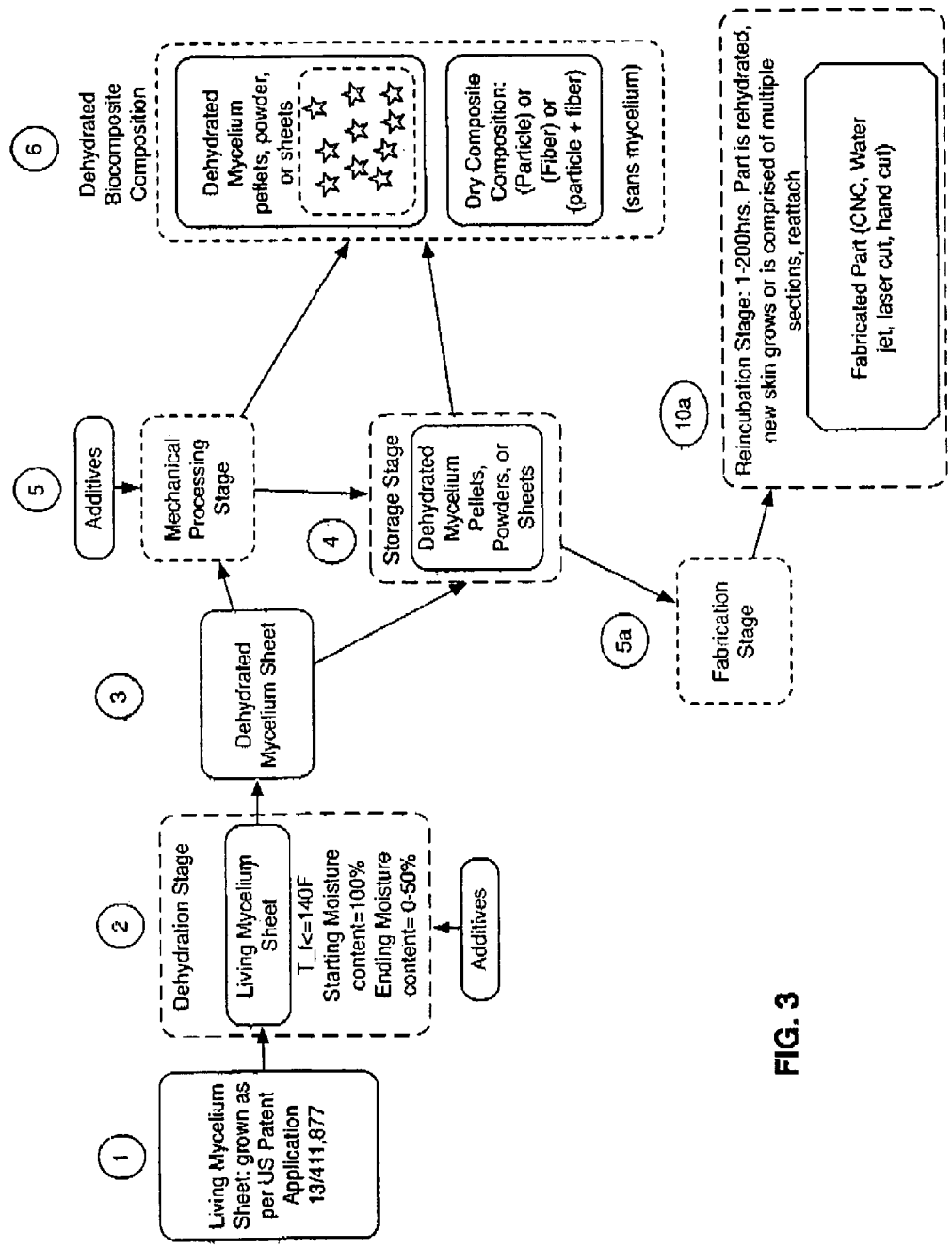
Figure 4:
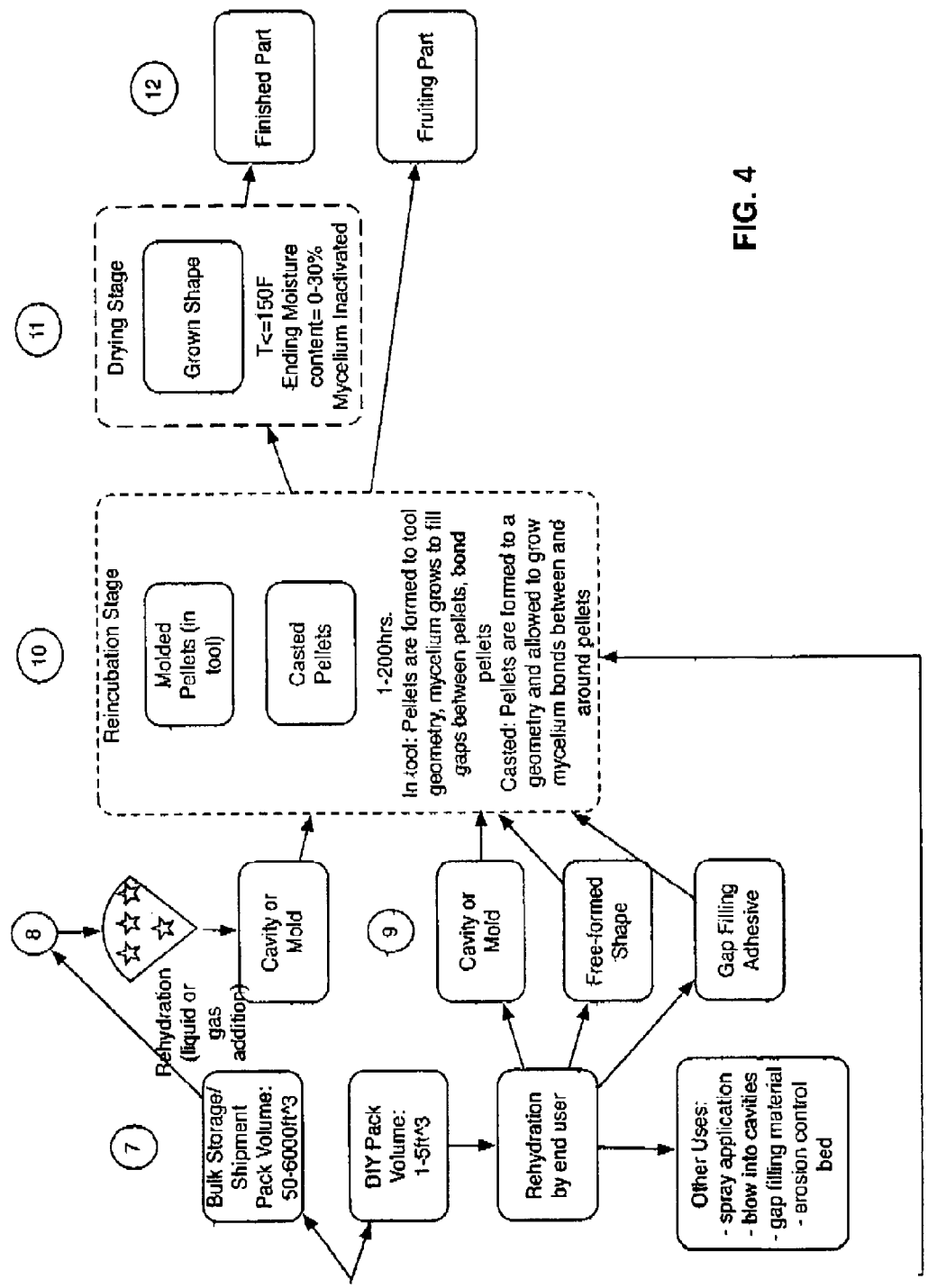
Figure 5A:
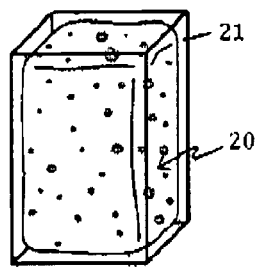
Figure 5B:
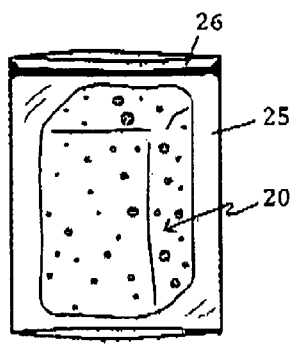
Figure 5C:
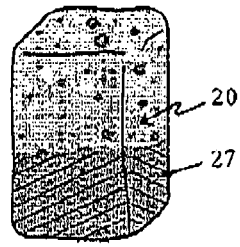
Figure 6A:
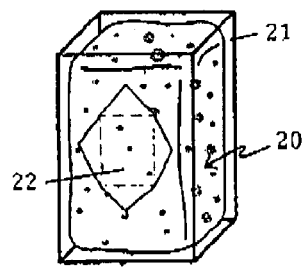
Figure 6B:
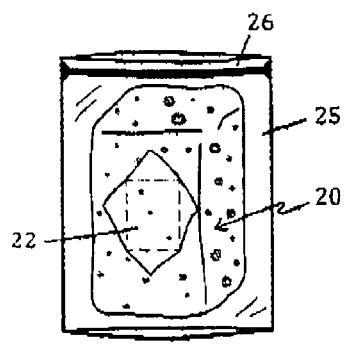
Figure 6C:
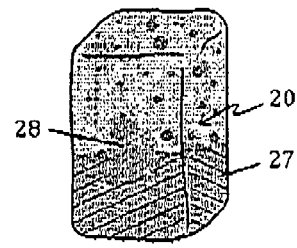
Figure 7A:
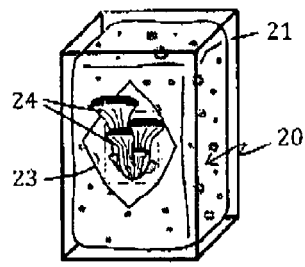
Figure 7B:
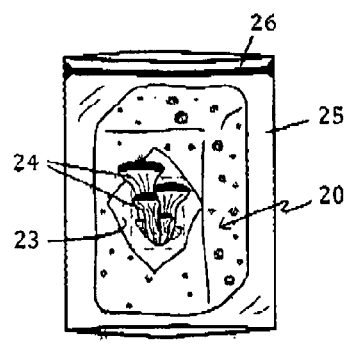
Figure 7C:
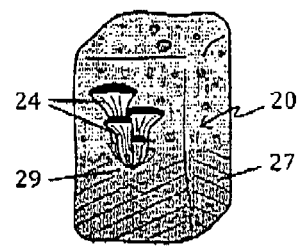

FIG. 3 schematically illustrates an alternative process for obtaining a living hydrated mycelium composite for making dehydrated mycelium elements in accordance with the invention;

FIG. 4 illustrates further steps in the method of FIG. 2;

FIG. 5A illustrates a perspective view of a container containing a dehydrated mycelium composite in accordance with the invention for retail sale;

FIG. 5B illustrates a perspective view of a modified container containing a dehydrated mycelium composite in accordance with the invention for retail sale;

FIG. 5C illustrates a perspective view of a dehydrated mycelium composite with a protective coating in accordance with the invention for retail sale;

FIG. 6A illustrates a view of the container of FIG. 5A in an opened condition;

FIG. 6B illustrates a view of the container of FIG. 5B in an opened condition;

FIG. 6C illustrates a view of the container of FIG. 5C in an opened condition;

FIG. 7A illustrates a view of the container of FIG. 6A after hydration and the growth of mushrooms;

FIG. 7B illustrates a view of the container of FIG. 6B after hydration and the growth of mushrooms;

FIG. 7C illustrates a view of the container of FIG. 6C after hydration and the growth of mushrooms.

Figure 1:
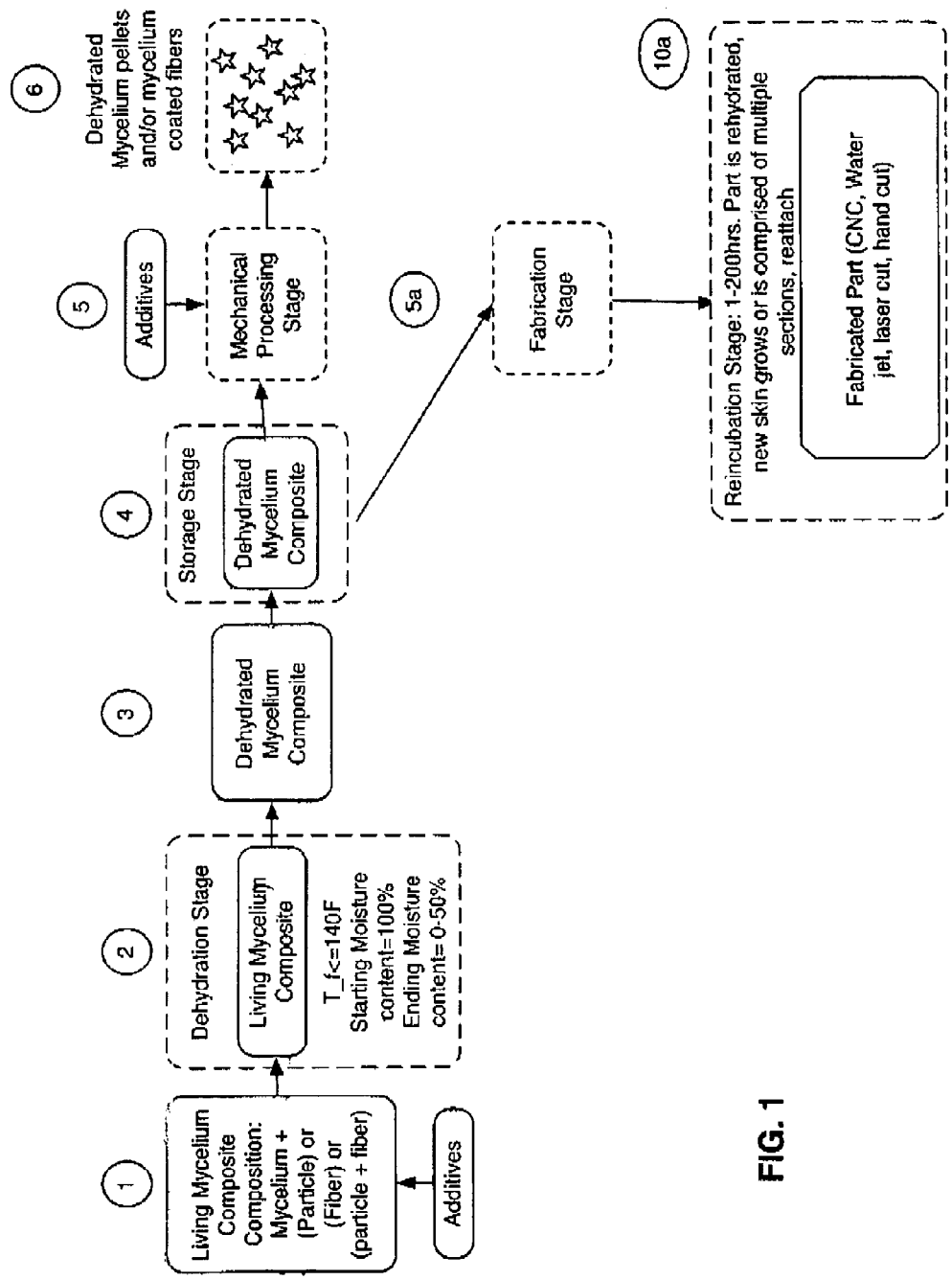
FIG. 1 illustrates initial steps in a method of making mycelium pellets in accordance with the invention.

Referring to FIG. 1, in accordance with a first step 1, a living mycelium composite is created. This can be a combination of mycelium and fibers, mycelium and particles, or both mycelium, particles, and fibers. Generally, a nutrient material is included with mycelium and fibers to promote mycelia tissue growth, such as described in Ser. No. 12/001,556, filed Dec. 12, 2007.

As described in Ser. No. 12/001,556, the mycelia tissue growth is sufficient for a fungal strain to digest the nutrient material, to grow hyphae and to allow the hyphae to form a network of interconnected mycelia cells through and around the at least one of the particles and fibers thereby bonding the particles and fibers together to form a cohesive whole (i.e. a self-supporting composite material) with a shape matching the internal shape of an enclosure containing the mycelium composite.

The mycelium may be a variation of fungi species or strain and may be natural, hybridized and/or a genetically modified organism (gmo) or a combination thereof.

The nutrient material may be added in solid or liquid form or in both forms. Also, the particles and the fibers may each be synthetic or natural or both.

Where the composite is created in a substrate, the substrate may be a natural product, a waste product, a chemical or synthetic product and the like. In other words, the substrate would be any suitable substrate for the creation of the composite.

In accordance with step 2, the living composite from step 1 is dehydrated at a temperature less than 140° F. from a starting moisture content of 100% to an ending moisture content of less than 50%.

Any suitable method of dehydration may be used. For example, freeze-drying; microwaving; air-flow/blowers; heat drying; supercritical fluids; mechanical methods; gas displacement of fluid; and fluid displaced by vacuum.

In accordance with step 3, the dehydrated mycelium composite is now in-active, and will no longer grow mycelial fibers, and will be incapable of producing mushrooms, primordia, or other tissue.

In accordance with step 4, the dehydrated mycelium composite is placed in storage and can be stored indefinitely, at temperatures ranging from −50° F. to 200° F. Lower moisture contents allow higher temperature storage ranges.

In accordance with step 5, the dehydrated mycelium composite from step 4 is mechanically processed into a plurality of particles or fibers in a mechanical processing stage. Additional additives, such as nutrients, growth enhancing compounds, binding agents, addition particles, additional fibers, or other materials may be added at this stage.

The added nutrients may include chemical or natural nutrients, flavor changers, smell changers and aesthetic changers.

Of note, nutrient addition may occur prior to dehydration; post-dehydration, pre-storage; post storage, pre-rehydration; or post-rehydration.

The dehydrated mycelium composite may also cohabitate with other organisms, i.e. with live seed.

Still further, the additives added to the dehydrated mycelium composite may include binding agents, additional particles, additional fibers, and growth enhancing compounds. As above, these additives may be added at any stage.

In accordance with step 6, the resulting particles and/or fibers geometry and size can be tuned to result in different densities and self adhesion characteristics. In the case of fibers, the fibers appear as being coated with mycelium.

Referring to FIG. 2, in accordance with step 7, the dehydrated mycelium composite particles and/or fibers from step 5 are stored in bulk, for example, in volumes of from 50 to 6000 cubic feet in step 7 or packed into a variety of containers or transport vessels for distribution including bulk shipments, super-sacks, tractor trailers, or small DIY packages of from 1 to 5 cubic feet (e.g. in 1 to 10 gallon containers).

Also, the dehydrated mycelium composite particles and/or fibers from step 5 may be used in other applications, such as for spray application, or by being blown into cavities and/or as gap filling material and in erosion control beds.

After storage and/or shipment, e.g, to a point of use, the dehydrated mycelium composite particles and/or fibers from step 7 are re-hydrated in accordance with step 8 to allow growth through the addition of moisture. Moisture can be added such that particles return to 100% moisture, or just enough moisture can be added (often less than 10% of the starting volume) such that the mycelium on the exterior of the particles re-activates and is able to grow into adjacent particles.

In accordance with step 8, the dehydrated mycelium composite particles and/or fibers are delivered into an aggregation hopper with moisture (water and/or gas) being added to the hopper, for example, by spraying. The re-hydrated mycelium composite particles and/or fibers are then delivered into a cavity or mold to be molded into elements, such as pellets in a tool or casted pellets.

In a similar manner, the dehydrated mycelium composite particles and/or fibers that are packaged in the small DIY packages can be rehydrated in a modified step 9 by the end user in any suitable manner and then placed in a cavity or mold to form an aggregated mass, or used as a free form shape or have an adhesive added to fill the gaps between the particles and/or fibers.

In accordance with step 10, the elements from step 9 are subject to a re-incubation stage for a period of time of from 1 to 200 hours in either a tool or are casted. For example, the molded pellets from the cavity or mold of step 9 are formed to a tool cavity geometry and the mycelium allowed to grow to fill the gaps between the pellets. Alternatively, the pellets are formed to a geometry and allowed to grow mycelium bonds between the pellets.

For the purpose of providing a product for the growth of mushrooms, the packages (i.e. containers) in which the dehydrated mycelium composite (particles and/or fibers) are sealed.

The sealed containers can be transported, for example, to a retail site for sale to patrons for the growing of mushrooms at home or elsewhere.

Referring to FIGS. 3 and 4, wherein like reference characters indicate like steps as above, in an alternative embodiment for creating a living dehydrated mycelium composite, a sheet of mycelium may be grown, for example, as described in co-pending U.S. patent application Ser. No. 13/411,877, and, once obtained, blended and added to a dry substrate, for example, of particles, fibers and/or particles and fibers as above. For example, the mycelium sheet may be chopped into pieces for blending with the particles and or fibers. The resultant mycelium composite may then be processed as above with the addition of nutrient material for promoting mycelium tissue growth and a subsequent dehydration step for into packages for retail sale.

As schematically illustrated, in accordance with step 1, a living mycelium sheet grown as described in U.S. Ser. No. 13/411,877 is obtained. Next, in accordance with steps 2 and 3, the mycelium sheet is dehydrated.

The dehydrated sheet of step 3 may then be placed in storage in accordance with step 4 or mechanically processed in accordance with step 5 and then placed in storage as in step 4.

The stored dehydrated mycelium pellets, powder and/or sheet from step 4 may then be fabricated in the fabrication stage of step 5a and subsequently subjected to the incubation stage for 1 to 200 hours, rehydrated wherein a new skin grows or wherein separate multiple sections are reattached and a fabricated part made, such as by CNC, water jet, laser cut and/or hand cut.

The stored dehydrated mycelium pellets, powder and/or sheet from step 4 as well as the dehydrated pellets, powder and/or sheets from step 5 may be processed in accordance with steps 6 through 12 as described above.

Alternatively, a dry composite composition of particles, fibers or particles and fiber without mycelium may be formed in step 6 and then further processed in accordance with steps 6 through 12 as described above.

As illustrated, after step 10, a re-incubated product may be directly processed to produce a fruiting part.

Referring to FIG. 5A, where the dehydrated mycelium composite is formed into a block 20 of cubic shape, a container 21 of cubic shape is provided for shipping and displaying the block 20. The container 21 is of similar shape and may be transparent, at least in part, to display the contents of the container 21.

Referring to FIG. 6A, the container 21 is provided with a removable means 22, such as a tab, that upon removal creates an opening 23 in the container 21, as indicated in FIG. 6A, to expose the composite block 20.

Referring to FIG. 7A, in order to initiate growth, the container 21 is opened by removal of the tab 22 to obtain access to the dehydrated composite material of the block 20 and in an environment at ambient temperatures, that is at normal room temperatures, at without need for a darkened place. Next, moisture is applied through the opening 23 in the container 21. For example, the moisture may be sprayed onto the exposed surfaces of the dehydrated composite material 21 or poured on. After a suitable period of time, one or more fruiting bodies (i.e. mushrooms) 24 will begin to grow through the opening 23 in the container 21 as indicated in FIG. 7A.

The fruiting bodies 24 may be harvested for use by any suitable cutting means. The container 20 may then be set aside to allow for a further crop of fruiting bodies 24 to be grown over time.

Alternatively, as shown in FIGS. 5B, 6B and 7B, wherein like reference characters indicate like parts as above, a container 25 in the form of a plastic pouch with a slide type of closure 26 may be used to contain the block 20 of dehydrated composite material. As above, the pouch 25 is provided with a removable tab 22 to create an opening 23 when removed.

Still further, as shown in FIGS. 5C, 6C and 7C, wherein like reference characters indicate like parts as above, as shown in FIG. 5C, the block 20 of dehydrated composite material may be encased in a protective coating 27, such as a wax coating, or a sprayed on coating, for transportation to a retail site for sale. In this embodiment, the coating 27 has an area 28 (see FIG. 6C) that can be removed or mechanically altered, such as by cutting or scraping the coating with a knife, to form an opening 29 (see FIG. 7C) for the growth of mushrooms 24.

Typically, the dehydrated composite material in the container will produce at least two growths (crops) of mushrooms over time before exhaustion.

The invention thus provides a relatively simple and economic method of making dehydrated mycelium elements that can be used for growing mushrooms.

What is claimed is:

1. A method of growing a fruiting body comprising the steps of
creating a living mycelium composite containing at least one of a combination of mycelium and fibers, mycelium and particles, and mycelium, particles and fibers; wherein said step of creating a living mycelium composite includes growing a sheet of mycelium, and thereafter blending and adding said sheet to a dry substrate of at least one of particles, fibers and/or particles and fibers to form said mycelium composite;
adding a nutrient material to said mycelium composite in an amount to promote mycelia tissue growth;
allowing the mycelium in said mycelium composite to digest the nutrient material, to grow hyphae and to allow the hyphae to form a network of interconnected mycelia cells through and around said fibers and/or particles of said at least one combination to form a cohesive whole with a shape matching the internal shape of an enclosure containing the mycelium composite;
thereafter dehydrating the mycelium composite to a moisture content of less than 50% by weight to deactivate the further growth of hyphae;
thereafter storing the dehydrated mycelium composite at a temperature in the range of from −50° F. to +200° F.;
pelleting the stored dehydrated mycelium composite into a plurality of particles,
aggregating the particles into a container, and
rehydrating the particles in the container to reactivate the mycelium therein
and to initiate growth of at least one fruiting body.

* * * * *